(12) United States Patent
Lim et al.

(10) Patent No.: US 11,291,704 B2
(45) Date of Patent: Apr. 5, 2022

(54) **COMPOSITION FOR PREVENTING OR TREATING OBESITY CONTAINING ETHANOLIC EXTRACT OF *RAMULUS MORI***

(71) Applicant: Korea University Research and Business Foundation, Seoul (KR)

(72) Inventors: Young Hee Lim, Seoul (KR); Seon Wook Hwang, Namyangju-si (KR); Jeung Keun Kim, Seoul (KR); Jun Ho Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 90 days.

(21) Appl. No.: 16/343,036

(22) PCT Filed: Oct. 18, 2017

(86) PCT No.: PCT/KR2017/011501
§ 371 (c)(1),
(2) Date: Apr. 18, 2019

(87) PCT Pub. No.: WO2018/074831
PCT Pub. Date: Apr. 26, 2018

(65) Prior Publication Data
US 2019/0262412 A1 Aug. 29, 2019

(30) Foreign Application Priority Data
Oct. 18, 2016 (KR) .................. 10-2016-0135251

(51) Int. Cl.
*A61K 36/605* (2006.01)
*A23L 33/105* (2016.01)

(52) U.S. Cl.
CPC .......... *A61K 36/605* (2013.01); *A23L 33/105* (2016.08); *A23V 2002/00* (2013.01)

(58) Field of Classification Search
None
See application file for complete search history.

(56) References Cited

FOREIGN PATENT DOCUMENTS

| CN | 1382478 | A | | 12/2002 |
|----|---------|---|---|---------|
| CN | 1970059 | A | * | 5/2007 |
| CN | 101664510 | A | * | 3/2010 |
| CN | 101664510 | A | | 3/2010 |
| CN | 102204966 | A | * | 10/2011 |
| CN | 103417634 | A | | 12/2013 |
| KR | 10-0237168 | B1 | | 1/2000 |
| KR | 10-0624488 | B1 | | 9/2006 |
| KR | 10-0813187 | B1 | | 3/2008 |

OTHER PUBLICATIONS

Kim, Hyun-Soo et al., "Effects of Ramulus mori Extract on Obesity and Lipid Metabolism in High Fat Diet Rats", *Journal of Korean Medicine*, Dec. 2002 vol. 23, No. 4, (pp. 64-72).
Park, Soo Yeon et al., "Postprandial hypoglycemic effects of mulberry twig and root bark in vivo and in vitro", *Journal of Nutrition and Health*, Feb. 2016, vol. 47, No. 1 (pp. 18-27).
International Search Report dated Jan. 24, 2018 in counterpart International Patent Application No. PCT/KR2017/011501 (2 pages in English and 2 pages in Korean).
Kim, Gun-Hee et al. "Comparison of extract and flavonoid-rich Fraction from mulberry on proliferation and lipid accumulation in 3T3-L1 adipocytes", *The FASEB Journal*, Experimental Biology 2014 Meeting Abstracts, vol. 28, Issue S1, LB392, https://doi.org/10.1096/fasebj.28.1_supplement.lb392, Apr. 1, 2014 (2 pages in English).
Chinese Office Action dated Sep. 7, 2021, in counterpart Chinese Patent Application No. 201780064498.X.

* cited by examiner

*Primary Examiner* — Terry A McKelvey
*Assistant Examiner* — Catheryne Chen
(74) *Attorney, Agent, or Firm* — NSIP Law

(57) ABSTRACT

The present invention relates to a composition for preventing or treating obesity containing an ethanolic extract of *Ramulus mori* as an active ingredient. As the present invention contains an ethanolic extract of *Ramulus mori*, extracted from natural substance *Ramulus mori*, as an active ingredient, the present invention may prevent or treat obesity by inhibiting lipid accumulation in adipocytes without any side effects to a human body and inhibiting preadipocytes from being differentiated into adipocytes.

5 Claims, 8 Drawing Sheets
(2 of 8 Drawing Sheet(s) Filed in Color)

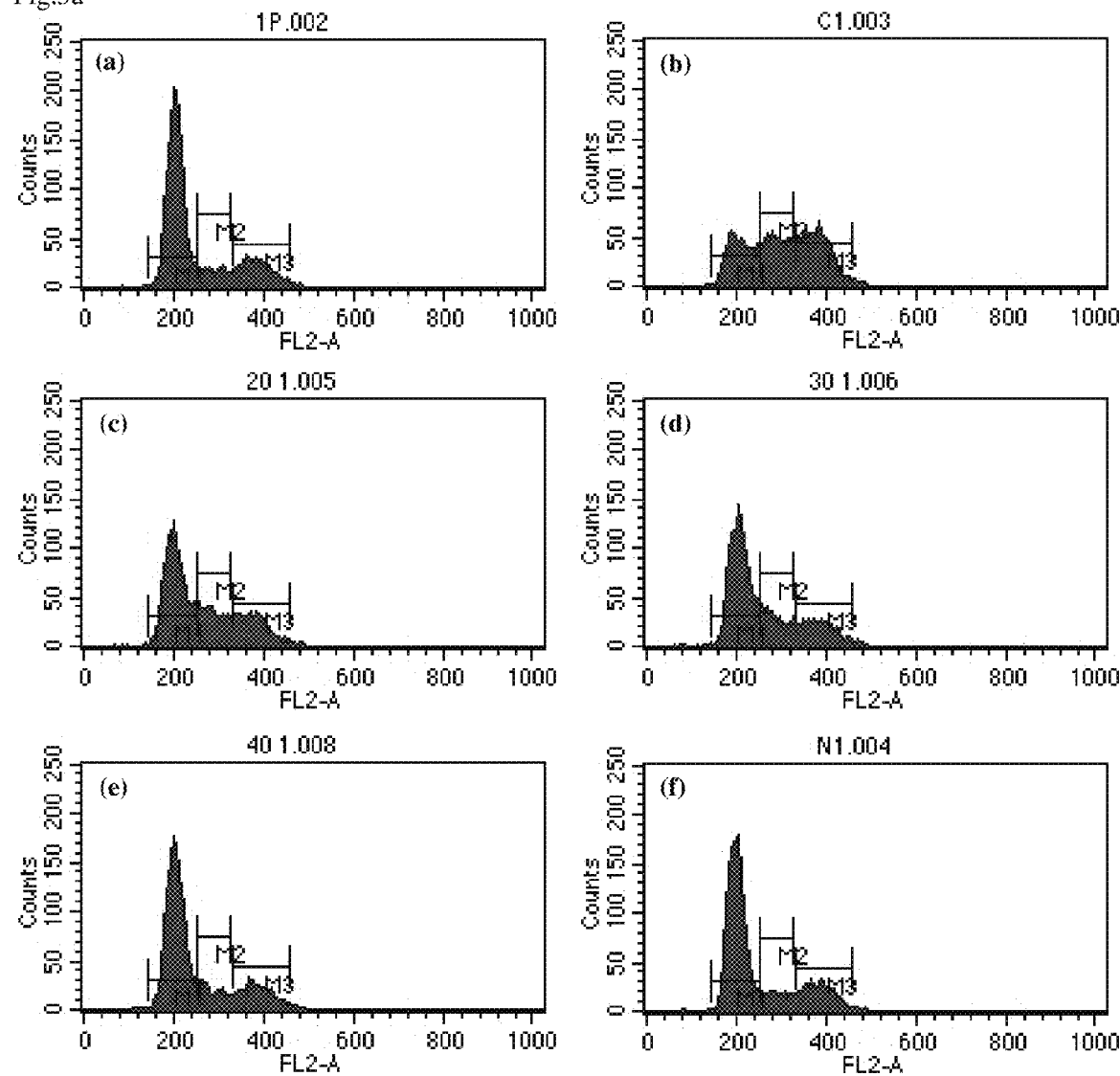

COMPOSITION FOR PREVENTING OR TREATING OBESITY CONTAINING ETHANOLIC EXTRACT OF *RAMULUS MORI*

CROSS REFERENCE TO RELATED APPLICATION(S)

This application is a U.S. national stage application of International Application No. PCT/KR2017/011501 filed on Oct. 18, 2017, which claims the benefit of Korean Patent Application No. 10-2016-0135251 filed on Oct. 18, 2016, in the Korean Intellectual Property Office, the entire disclosures of which are incorporated herein by reference for all purposes.

TECHNICAL FIELD

The present disclosure relates to a composition containing an ethanolic extract of *Ramulus mori* for preventing or treating obesity.

BACKGROUND ART

Body lipid accumulation is caused by excess lipid produced by adipocytes. Lipid accumulation by the promotion of adipocyte differentiation causes obesity, which is known to be a cause of various diseases, such as type 2 diabetes, hypertension, and vascular diseases (HAJER, G. R., Van Haeften, T. W., Visseren, F. L., 2008. Adipose tissue dysfunction in obesity, diabetes, and vascular diseases. European heart journal, 29(24), 2959-2971). There are 2.1 billion obese people in the world in 2012, and the predicted number of obese people in 2030 will increase to 3.3 billion. Various anti-obesity products are currently being developed and marketed, and the scale of the anti-obesity product market is continuously increasing. However, many commercial anti-obesity medicines currently on the market are reported to show side effects (e. g., increasing the risk of developing mental illness, and causing myocardial infarction, stroke, and gastrointestinal side effects), and thus the product licenses thereof are being canceled (Kang, J. G. and Park, C., 2012. Anti-obesity drugs: a review about their effects and safety. Diabetes & metabolism journal, 36(1), 13-25). Therefore, studies are currently being actively conducted on alternative therapies showing obesity suppressing effects derived from natural products in consideration of safety or the like. (Lai, C., Wu, J., Pan, M., 2015. Molecular mechanism on functional food bioactives for anti-obesity. Current Opinion in Food Science, 2, 9-13). Natural functional raw materials, which are approved for the effect of body lipid reduction by the Korea Food and Drug Administration and currently being marketed, include *Garcinia cambogia* bark extracts, *Colleus foscoli* extracts, sesame leaf extracts, green mate extracts, composites of soybean embryo extracts and others, green tea extracts, lemon balm extract mix powders, mate hot-water extracts, *Gynostemma pentaphyllum* leaf ethanolic extract powders, fingerroot extract powders, lactoferrin, composite extracts of seaweed and others, pu-ert tea extracts, wild mango seed extracts, green coffee bean extracts, composites of fermented vinegar and pomegranate, chitosan, chitooligosaccharides, black soybean peptide composites, L-carnitine tartrate, conjugated linoleic acid, composite extracts of hibiscus and others, and the like (Recognition status of functional raw materials for health functional foods, Korea Food and Drug Administration, 2015).

Adipocytes are the cells that accumulate lipids in adipose tissue, and play a role in maintaining the homeostasis of body energy metabolism. Obesity is caused as a result of excessive accumulation of adipose tissue composed of adipocytes. Therefore, adipocyte differentiation causes lipid accumulation, which is closely associated with obesity (Ristow, M., Muller-Wieland, D., Pfeiffer, A., Krone, W., Kahn, C. R., 1998. Obesity associated with a mutation in a genetic regulator of adipocyte differentiation. New England Journal of Medicine, 339(14), 953-959). Adipocytes are derived from a mesenchymal precursor, which differentiates into adipocytes via preadipocytes, and during the differentiation, adipocytes accumulate body lipids through morphological and biochemical changes thereof. Adipocyte differentiation is induced by expression changes of a series of genes, which are characteristically expressed in adipose tissue cells, and is regulated by the expression of transcription factors acting on regulatory sites of the genes. Insulin is a hormone that induces adipocyte differentiation, and is a main external factor involved in the regulation of adipocyte metabolism. During adipocyte differentiation, the expression of transcription factors, such as CCAAT enhancer-binding-proteins (C/EBP) family, peroxisome-proliferators activated-receptor-$\gamma$ (PPAR-$\gamma$), and sterol regulatory element binding protein-1 (SREBP-1), is increased, and these transcription factors induce mutual transcription, leading to adipocyte differentiation. Therefore, obesity studies are needed using natural products, which inhibit the expression of these transcription factors and have no side effects.

DETAILED DESCRIPTION OF THE INVENTION

Technical Problem

An aspect of the present disclosure is to provide a composition for prevention or treatment of obesity, the composition containing an ethanolic extract of *Ramulus mori* suppressing lipid accumulation or inhibiting adipocyte differentiation.

However, problems to be solved by the present disclosure are not limited to the above-mentioned problems, and other problems not mentioned will be clearly understood by a person skilled in the art from the following description.

Technical Solution

In accordance with an aspect of the present disclosure, there is provided a composition containing an ethanolic extract of *Ramulus mori* as an active ingredient for prevention or treatment obesity.

The ethanolic extract of *Ramulus mori* may suppress lipid accumulation.

The ethanolic extract of *Ramulus mori* may inhibit adipocyte differentiation.

The ethanolic extract of *Ramulus mori* may inhibit the expression of at least one transcription factor selected from the group consisting of peroxisome-proliferators activated-receptor-$\gamma$ (PPAR-$\gamma$), CCAAT/enhancer-binding protein-$\alpha$ (C/EBP-$\alpha$), and sterol regulatory element binding protein-1 (SREBP-1).

The composition may be a pharmaceutical composition.

The composition may further contain a pharmaceutically acceptable carrier.

In accordance with another aspect of the present disclosure, there is provided a food composition containing an ethanolic extract of *Ramulus mori* as an active ingredient for prevention or treatment obesity.

Advantageous Effects

The composition for prevention or treatment of obesity of the present disclosure contains, as an active ingredient, an ethanolic extract of *Ramulus mori*, which is extracted from the natural product *Ramulus mori*, and thus can prevent or treat obesity by suppressing lipid accumulation in adipocytes or inhibiting the differentiation of preadipocytes into adipocytes, without side effects on the human body.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

FIGS. 5a and 5b show FACS results of adipocytes treated with an ethanolic extract of *Ramulus mori* according to an embodiment.

BEST MODE FOR CARRYING OUT THE INVENTION

Figure 1:
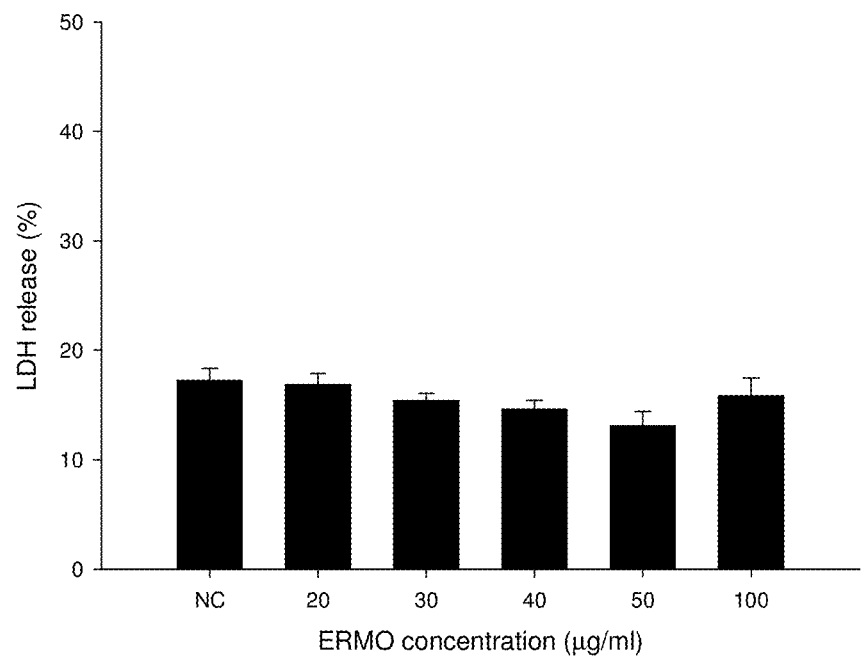
FIG. 1 is a graph showing the degree of cytotoxicity in 3T3-L1 cells treated with an ethanolic extract of *Ramulus mori* according to an embodiment.

Hereinafter, embodiments will be described in detail with reference to the accompanying drawings. Like reference numerals provided in the drawings indicate like elements.

Various modifications may be made to the embodiments described below. It should be understood that the embodiments described below are not construed to limit forms of implementation and include all modifications, equivalents, and alternatives to the embodiments.

The terminology used in the embodiments is for the purpose of merely describing particular embodiments and is not intended to limit the embodiments. As used herein, the singular forms are intended to include the plural forms as well, unless the context clearly indicates otherwise. It will be further understood that the term "comprise/include", "have," or the like, when used in this specification, are intended to specify the presence of features, figures, steps, operations, elements, components or combinations thereof, described in the specification, but do not exclude in advance the possibility of the presence or addition of one or more other features, figures, steps, operations, elements, components or combinations thereof, Unless defined otherwise, all the terminologies used herein, including technical or scientific terminologies have the same meaning as those commonly understood by a person skilled in the art to which the embodiments belong. Terminologies as defined in commonly used dictionaries should be interpreted to have the same meaning as those of the terminologies in context in the related descriptions, and shall not be interpreted in an idealized or overly formal sense, unless expressly so defined herein.

In the description with reference to the accompanying drawings, the same elements will be designated by the same reference numerals, regardless of the reference numerals, and the overlapping description thereof will be omitted. Furthermore, in the description of embodiments, the detailed description of related well-known techniques will be omitted when it is deemed that such description will render the gist of embodiments unnecessarily vague.

According to an embodiment, provided is a composition containing an ethanolic extract of *Ramulus mori* as an active ingredient for prevention or treatment obesity. Especially, the ethanolic extract of *Ramulus mori* can suppress the lipid accumulation in adipocytes and inhibit the differentiation of preadipocytes into adipocytes.

The "*Ramulus mori*" used herein is a material recorded as a food raw material, and has no side effects (e. g., hepatoxicity) even when used for a long period or in a large amount. The composition containing an ethanolic extract of *Ramulus mori* of the present disclosure can sufficiently attain a lipid accumulation suppressing or adipocyte differentiation inhibiting effect even when administered orally.

In accordance of an aspect, the ethanolic extract of *Ramulus mori* can inhibit the expression of at least one transcription factor selected from the group consisting of peroxisome proliferator-activated receptor-γ (PPAR-γ), CCAAT/enhancer-binding protein-α (C/EBP-α), or sterol regulatory element binding protein-1 (SREBP-1). Referring to Example 5, it can be confirmed that the expression of PPAR-γ, C/EBP-α, and SREBP-1, which are genes associated with adipocyte differentiation, is reduced in adipocytes treated with the ethanolic extract of *Ramulus mori*. As the concentration of the ethanolic extract of *Ramulus mori* increases, the expression of the genes PPAR-γ, C/EBP-α, and SREBP-1 may also decrease.

The composition of the present disclosure may be a pharmaceutical composition, and therefore, may further contain a pharmaceutically acceptable carrier.

As used herein, the term "pharmaceutically acceptable carrier" refers to a pharmaceutically acceptable material, composition, or vehicle, such as a liquid or solid filler, a diluent, an excipient, a solvent, or an encapsulation material, which is involved in the transfer or transport of any target composition or ingredient from one organ or part of the body to another organ or part of the body. The composition of the present disclosure may further contain, for administration, a pharmaceutically acceptable carrier, excipient, or diluent, in addition to the above-mentioned active ingredient. Examples of the carrier, excipient, and diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

In addition, the composition of the present disclosure can be formulated in the form of: an oral formulation, such as a powder, granules, a tablet, a capsule, a suspension, an emulsion, a syrup, or an aerosol; a preparation for external application; a suppository; or a sterile injectable solution, according to usual methods, respectively. Specifically, the composition of the present disclosure, when formulated, may be prepared by using a diluent or excipient, such as a filler, an extender, a binder, a wetting agent, a disintegrant, or a surfactant, which are commonly used. A solid preparation for oral administration may include, but not limited to, a tablet, a pill, a powder, granules, a capsule, and the like. Such a solid preparation may be prepared by mixing at least one excipient, for example, starch, carbonate calcium, sucrose, lactose, or gelatin, with the composition. In addition, lubricants, such as magnesium stearate and talc, may be used beside simple excipients. A liquid preparation for oral administration may include, but is not limited to, a suspension, a liquid for internal use, an emulsion, a syrup, and the like. The liquid preparation may be prepared by adding not only a simple diluent frequently used, such as water or liquid paraffin, but also several excipients, such as a wetting agent, a sweetener, an aromatic agent, and a preservative. A preparation for parenteral administration may include a sterile aqueous solution, a non-aqueous solvent, a suspension, an emulsion, a lyophilized preparation, and a suppository. The non-aqueous solvent and the suspension may include propylene glycol, polyethylene glycol, vegetable oils such as olive oil, injectable esters such as ethylolate, and the like. A base material for the suppository may include Witepsol, macrogol, Tween 61, cacao butter, laurin butter, glycerogelatin, and the like.

Furthermore, the composition of the present disclosure may be administered orally or parenterally (e. g., intravenous, subcutaneous, intraperitoneal, or topical application) according to the desired method, and preferably may be orally administered. The "*Ramulus mori*" used herein is a material recorded as a food raw material, and has no side effects (e. g., hepatotoxicity) even when used for a long period or in a large amount, and can sufficiently attain a lipid accumulation suppressing or adipocyte differentiation inhibiting effect even when orally administered. The dose may vary depending on the condition and body weight of a patient, severity of disease, form of a drug, and manner and period of administration, but may be properly selected by a person skilled in the art. The composition may be administered in a single dose or may be divided into multiple doses per day according to the need. Also, the composition may be used alone, or in combination with methods using surgery, hormone therapy, pharmacotherapy, and biological response regulators, for the prevention or treatment of intestinal diseases.

Meanwhile, the composition for prevention or treatment of an inflammatory intestinal disease of the present disclosure may be a food composition as well as a pharmaceutical composition. The composition may be added as it is or may be used together with other foods or food ingredients.

Examples of the food may include meat, sausage, bread, chocolate, candies, snacks, cookies, pizza, ramen, other noodles, gums, dairy products including ice cream, various soups, beverages, teas, drinks, alcoholic beverages, vitamin complexes, and the like, and encompasses all health functional foods in a typical sense.

The composition of the present disclosure may contain various flavorants or natural carbohydrates as additional ingredients, like in common health functional foods. The natural carbohydrates may be monosaccharides, such as glucose and fructose, disaccharides such as maltose and sucrose, polysaccharides such as dextrin and cyclodextrin, and sugar alcohols, such as xylitol, sorbitol, and erythritol. The sweetener may include natural sweeteners, such as thaumatin and a stevia extract, and synthetic sweeteners, such as saccharin and aspartame.

The composition of the present disclosure may contain various nutrients, vitamins, electrolytes, flavorants, colorants, pectic acid and salts thereof, alginic acid and salts thereof, organic acids, protective colloid thickeners, pH adjusters, stabilizers, stabilizing agents, preservatives, glycerins, alcohols, carbonating agents used in carbonated drinks, and the like. Besides, the composition of the present disclosure may contain fruit flesh for manufacturing natural fruit juice, fruit juice drink, and vegetable drink. These ingredients may be used independently or in combination.

In the following examples, a toxicity test on cells was conducted before it was investigated whether the ethanolic extract of *Ramulus mori* was helpful in suppressing lipid accumulation and inhibiting adipocyte differentiation. 3T3-L1 preadipocytes (lipid precursor cells) (American Type Culture Collection, USA) were administered with materials, and then tested for the suppression of lipid droplet accumulation and the inhibition of adipocyte differentiation.

Example 1: Preparation of Ethanolic Extract of *Ramulus mori*

1 Kg of finely cut *Ramulus mori* was prepared. The *Ramulus mori* was cleanly washed with distilled water, and then 8,000 mL of 80% ethanol for alcoholic beverages was added thereto, followed by extraction for 48 hours in an ultrasonic cleaner (H0429115, Hwashin Instrument Co.). The ethanolic extract having finished the extraction was filtered under reduced pressure using GFC filter paper (Cat No. 1822-047, Whatman), and then concentrated under reduced pressure to about 500 mL by using a rotary vacuum evaporator (N-1000, Eyela). The concentrated extract was frozen in a cryogenic freezer (DF8520, Ilshin Lab Co.) at $-80°$ C., and then freeze-dried for 48 hours using a freeze dryer (FD8512, Ilshin Lab Co.), thereby preparing the ethanolic extract of *Ramulus mori* to have a powder form.

Example 2: Preparation of Adipocytes

3T3-L1 preadipocytes (American Type Culture Collection, USA) were incubated in an atmosphere of 5% $CO_2$ and 37° C. using Dulbecco's modified Eagle medium (DMEM) (HyClone, Logan, Utah, USA) containing 10% bovine calf serum (BCS) and 1% penicillin-streptomycin. The medium was exchanged with a fresh medium every two days while the cells were incubated, and tests were conducted on the suppression of lipid droplet accumulation and the inhibition of differentiation into adipocytes.

Example 3: Cytotoxicity Evaluation

For evaluation of cytotoxicity of an ethanolic extract of *Ramulus mori* (ERMO), the degree of lactate dehydrogenase (LDH) release in 3T3-L1 cells was used as an indicator.

3T3-L1 cells were inoculated in a 96-well plate at a concentration of $5 \times 10^3$ cells/well, and then incubated for 24 hours. In addition, a sample was added to the medium, and after 1 hour, the cytotoxicity was measured using an EZ-LDH cytotoxicity assay kit (Daeil Lab Service Co., Seoul, Korea). Cytotoxicity was calculated according to the following equation.

$$\% \text{ LDH release} = (\text{LDH in culture medium}/\text{Total LDH}) \times 100.$$

The ethanolic extract of *Ramulus mori* was prepared with concentrations of 20 μg/ml, 30 μg/ml, 40 μg/ml, 50 μg/ml, and 100 μg/ml, each of which was then treated on 3T3-L1 cells. The degree of LDH release was measured according to the concentration of the ethanolic extract of *Ramulus mori*.

FIG. 1 is a graph showing the degree of cytotoxicity in 3T3-L1 cells treated with an ethanolic extract of *Ramulus mori* according to an embodiment.

Referring to FIG. 1, the degrees of LDH release according to the concentration of the ethanolic extract of *Ramulus mori* were as follows: 20 µg/ml (16.9±1.0%), 30 µg/ml (15.8±1.6%), 40 µg/ml (14.6±0.8%), and 50 µg/ml (13.1±1.3%), 100 µg/ml (14.6±0.8%). No greatly significant LDH release was observed in most cases when compared with the control (17.2±1.1%). Regardless of the results showing no significant LDH release, it could be confirmed that the ethanolic extract of Ramulus mori had no cytotoxicity.

Example 4: Lipid Accumulation Evaluation

For induction of 3T3-L1 cells into adipocytes, the cells were treated with MDI (5 µg/ml insulin, 0.5 mM IBMX, and 1.0 µM dexamethasone) in DMEM containing 10% FBS and 1% penicillin-streptomycin, followed by induction of differentiation for 2 days. The differentiated 3T3-L1 cells were washed with physiological buffered saline (PBS), and then fixed with 10% formalin for 1 hour. The fixed cells were washed twice with $ddH_2O$, treated with 60% isopropanol for 5 minutes, and then stained with Oil red O solution (dissolved in 60% isopropanol) for 10 minutes. After staining, the cells were washed four times with $ddH_2O$, and de-stained with 100% isopropanol for 10 minutes, and then the cells were observed using a microscope and measured for absorbance at 500 nm.

Figure 2:
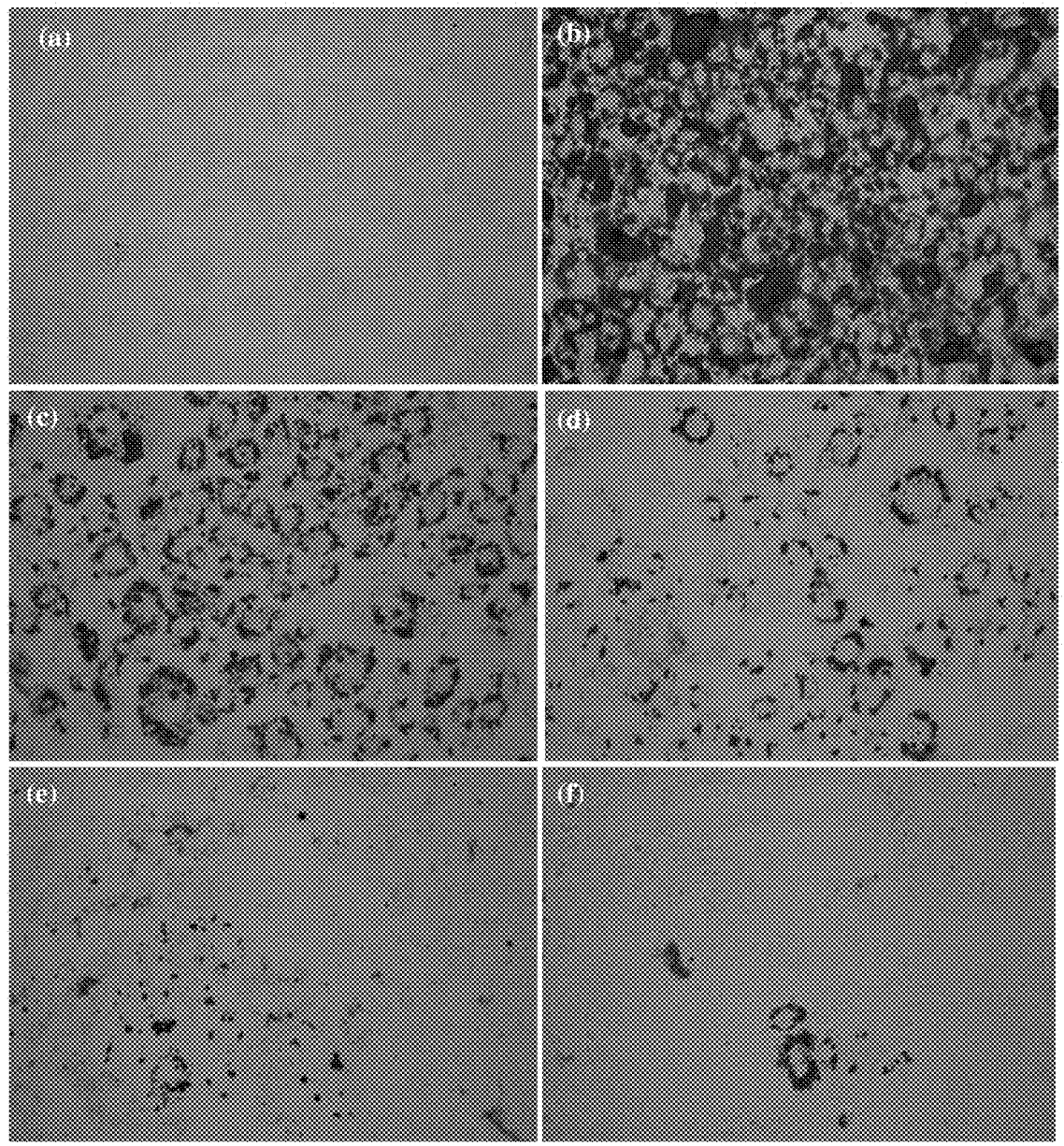
FIG. 2 shows images illustrating lipid droplets in adipocytes treated with an ethanolic extract of *Ramulus mori* according to an embodiment.

FIG. 2 shows images illustrating lipid droplets in adipocytes treated with an ethanolic extract of Ramulus mori according to an embodiment.

Referring to FIG. 2, it was observed that the lipid droplets was remarkably reduced dependent on the concentration of the ethanolic extract of Ramulus mori in the groups treated with the ethanolic extract of Ramulus mori.

The result of the sample treated with only DMSO used as a solvent was converted to 100%, and quantitatively measured for lipids.

Figure 3:
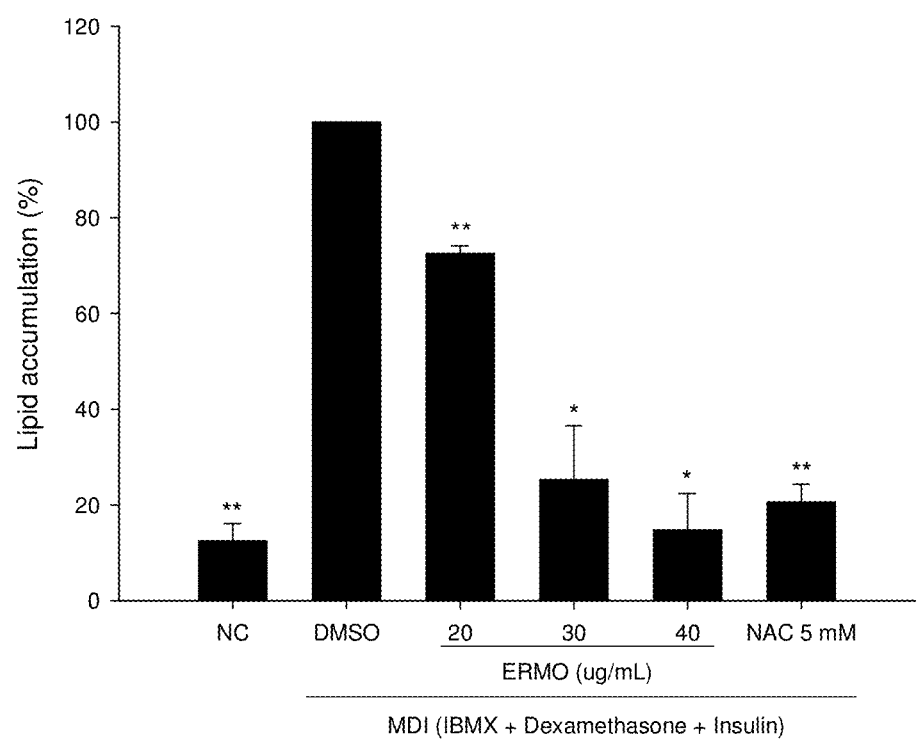
FIG. 3 is a graph showing lipid accumulation in adipocytes treated with an ethanolic extract of *Ramulus mori* according to an embodiment.

FIG. 3 is a graph showing lipid accumulation in adipocytes treated with an ethanolic extract of Ramulus mori according to an embodiment.

Referring to FIG. 3, it was observed that the lipid accumulation was reduced in the groups treated with ethanolic extracts of Ramulus mori (20 µg/ml (72.5±1.6%), 30 µg/ml (25.3±11.3%), and 40 µg/ml (14.7±7.7%)), indicating similar degrees of lipid accumulation to the group treated with n-acetyl cysteine (NAC, 5 mM) (20.6±3.7%). Therefore, it could be seen that the ethanolic extract of Ramulus mori (ERMO) had an excellent lipid accumulation inhibitory effect on adipocytes.

Example 5: Measurement of Expression of Adipocyte Differentiation-Related Genes

Total mRNA was extracted from the differentiated cells by using AccuZol reagent (Bioneer, Daejun, Korea), and then quantified with NanoDrop (ND-1000, Thermo Scientific). 1 µg of mRNA was reversely transcribed into cDNA by using the Revert Aid First Strand cDNA synthesis kit (Thermo Scientific, Waltham, Mass., USA). Quantitative real-time RT-PCR (qPCR) was performed using a StepOne Plus Real-Time PCR System (Applied Biosystems, Foster City, Calif., USA). The PCR was performed at 95° C. for 10 minutes, and then 40 cycles of 95° C. for 15 seconds and 60° C. for 1 minute. The β-actin gene was used as an endogenous control, and the expression level of a non-treated sample (negative control) was assumed to be 1, and relative quantification ($2^{-\Delta\Delta C_t}$ method) was carried out.

Figure 4A:
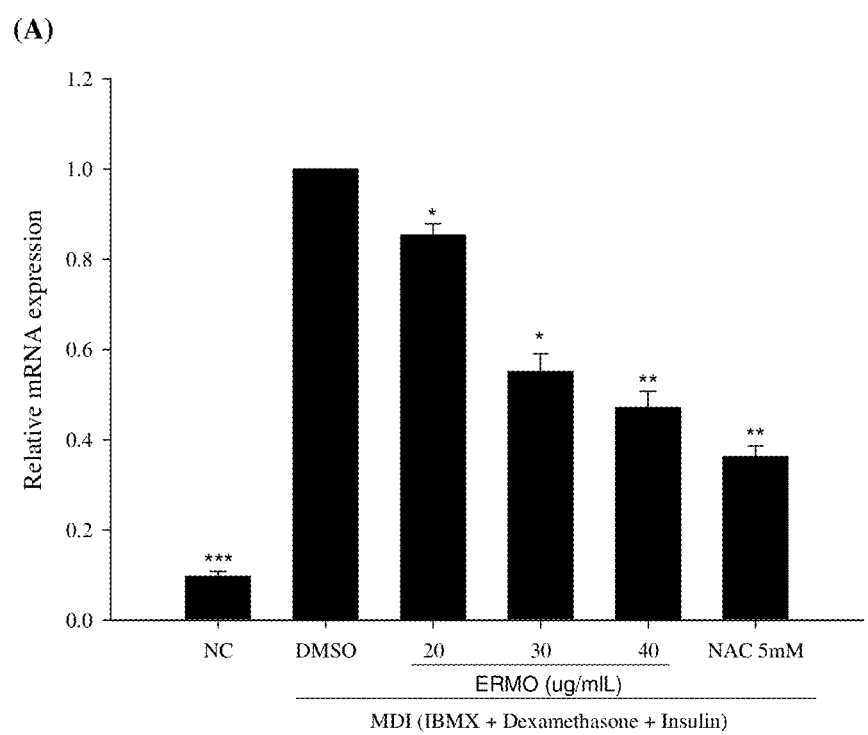
FIGS. 4a is a graph showing expression levels of the gene PPAR-γ associated with adipocyte differentiation in adipocytes treated with an ethanolic extract of *Ramulus mori* according to an embodiment.
Figure 4B:
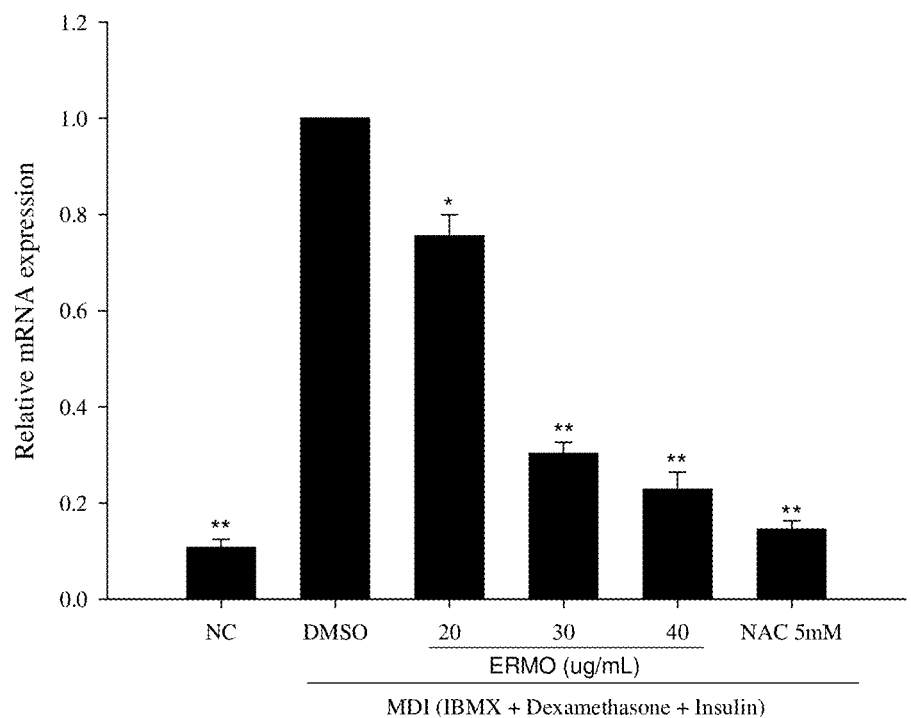
Figure 4C:
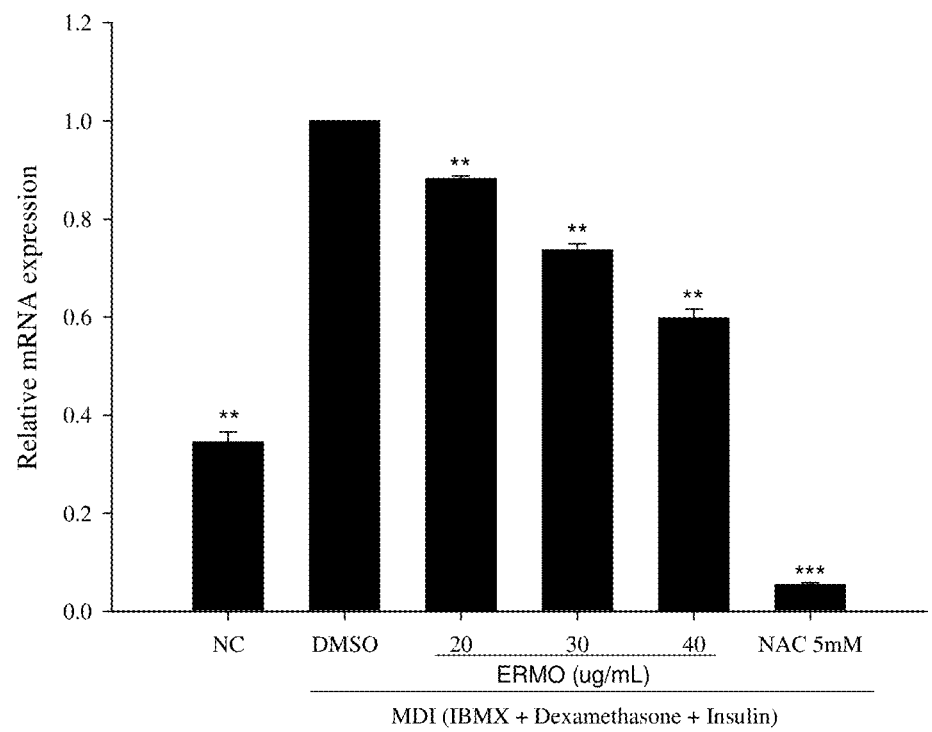

FIGS. 4a to 4c are graphs showing expression levels of genes associated with adipocyte differentiation in adipocytes treated with an ethanolic extract of Ramulus mori according to an embodiment.

Referring to FIGS. 4a to 4c, for evaluation of the inhibition of an ethanolic extract of Ramulus mori (ERMO) on expression of adipocyte differentiation-related genes, the differentiation of 3T3-L1 cells was induced by MDI, and then gene expression was subjected to qPCR analysis. As a result, it could be seen that the expression of all of peroxisome proliferator-activated receptor-γ (PPAR-γ), CCAAT/enhancer-binding proteins-α (C/EBP-α), and sterol regulatory element-binding protein-1 (SREBP-1) was reduced dependent on the concentration of the ethanolic extract of Ramulus mori (ERMO).

More specifically, the result of the sample treated with only DMSO used as a solvent was converted into 1 and the relative levels of expression were compared. As a result, it could be confirmed that referring to FIG. 4a, the expression of PPAR-γ was reduced to 20 µg/ml (0.85±0.03), 30 µg/ml (0.55±0.04), and 40 µg/ml (0.47±0.04); referring to FIG. 4b, the expression of C/EBP-α was reduced to 20 µg/ml (0.76±0.04), 30 µg/ml (0.30±0.02), and 40 µg/ml (0.23±0.04); and referring to FIG. 4c, SREBP-1 was reduced to 20 µg/ml (0.88±0.001), 30 µg/ml (0.74±0.01), and 40 µg/ml (0.60±0.02).

Example 6: Evaluation of Inhibition of Adipocyte Differentiation

For evaluation of the inhibition of adipocyte differentiation, 3T3-L1 cells were incubated in a 100-mm dish, and then an ethanolic extract of Ramulus mori was added thereto to induce cell differentiation for 18 hours. After the cells were collected, the cells were fixed with 70% ethanol at 4° C. for at least 2 hours, and then were washed with PBS. Thereafter, the cells were collected through centrifugation at 300×g for 5 minutes. The fixed cells were stained using the FxCycle PI/RNase Staining solution (Invitrogen Molecular Probes, Carlsbad, Calif., USA) at room temperature for 30 minutes. The stained cells were analyzed using flow cytometry (BD Caliber, Franklin Lakes, N.J., USA).

That is, for evaluation of the inhibition of the ethanolic extract of Ramulus mori (ERMO) on the differentiation of 3T3-L1 cells into adipocytes, the differentiation of 3T3-L1 cells were induced by MDI, and then the cells in an initial procedure of differentiation were subjected to fluorescence-activated cell sorting (FACS) analysis, and the cell proportion at each phase was quantified.

Figure 5B:
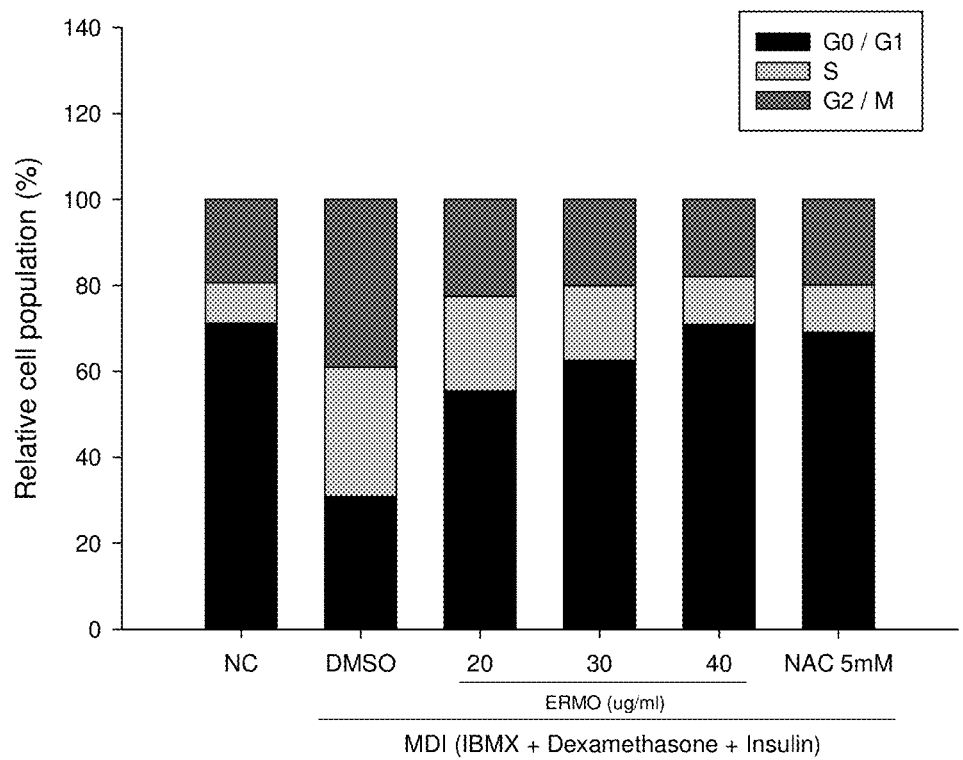

FIGS. 5a and 5b show FACS results of adipocytes treated with an ethanolic extract of Ramulus mori according to an embodiment.

It could be seen from the FACS results in FIG. 5a that the cells at the S phase were reduced and the cells in the $G_0/G_1$ period were increased by the treatment with the ethanolic extract of Ramulus mori. Referring to FIG. 5b, it could also be seen from the quantification of FACS results that the cells in the $G_0/G_1$ period were increased dependent on the concentration of the ethanolic extract of Ramulus mori (ERMO) by the treatment with the ethanolic extract of Ramulus mori (ERMO) compared with the group treated with only DMSO used as a solvent. More specifically, the cell population proportion in the $G_0/G_1$ period was 30.86% in the sample treated with only DMSO used as a solvent, and was increased to 55.41, 62.49, and 70.78% in the groups treated with the ethanolic extract of Ramulus mori (ERMO) at 20, 30, and 40 µg/ml, respectively. These results mean that the differentiation of 3T3-L1 preadipocytes was stopped in the G0/G1 period by the treatment with the ethanolic extract of *Ramulus mori* (ERMO), and therefore, it could be confirmed that the ethanolic extract of *Ramulus mori* (ERMO) inhibited the differentiation of 3T3-L1 cells into adipocytes.

Statistical analysis used throughout the examples of the present disclosure was performed using SigmaPlot Version 10.0 and SPSS version 21, and if a significance was observed when the one-way analysis of variation (ANOVA) was performed, the Dunnett's t-test was performed to identify a test group with a significant difference from the solvent control (*p<0.05).

Although the examples have been described by the limited examples and drawings as set forth above, a person skilled in the art could make various corrections and modifications from the above description. For example, appropriate results can be achieved even though the described techniques are performed in a different order from the described method, and/or the described elements may be coupled or combined in a different form from the described methods, or may be replaced or substituted with other elements or equivalents.

Therefore, other embodiments, other examples, and equivalents to the claims are also within the scope of the following claims.

The invention claimed is:

1. A method of treating and/or preventing obesity in a mammal in need thereof, said method comprising:
   administering an ethanolic extract of *Ramulus mori* to the mammal; and
   confirming an inhibition of differentiation of a preadipocyte into an adipocyte in the mammal.

2. The method of claim 1, wherein the ethanolic extract of *Ramulus mori* is ultrasonic ethanolic extract.

3. The method of claim 1, wherein the ethanolic extract of *Ramulus mori* suppresses lipid accumulation.

4. The method of claim 1, wherein the ethanolic extract of *Ramulus mori* inhibits adipocyte differentiation.

5. The method of claim 1, wherein the ethanolic extract of *Ramulus mori* inhibits the expression of at least one transcription factor selected from the group consisting of peroxisome proliferator-receptor-$\gamma$ (PPAR-$\gamma$), CCAAT/enhancer-binding protein-$\alpha$ (C/EBP-$\alpha$), and sterol regulatory element binding protein-1 (SREBP-1).

* * * * *